United States Patent
Shantha

(10) Patent No.: US 9,072,613 B2
(45) Date of Patent: Jul. 7, 2015

(54) DEVICE FOR SNORING AND OBSTRUCTIVE SLEEP APNEA TREATMENT

(76) Inventor: Totada R Shantha, Stone Mountain, GA (US)

(*) Notice: Subject to any disclaimer, the term of this patent is extended or adjusted under 35 U.S.C. 154(b) by 384 days.

(21) Appl. No.: 13/530,693

(22) Filed: Jun. 22, 2012

(65) Prior Publication Data

US 2012/0255561 A1 Oct. 11, 2012

(51) Int. Cl.
| | |
|---|---|
| A61F 5/56 | (2006.01) |
| A61C 5/00 | (2006.01) |
| A61M 25/02 | (2006.01) |
| A61C 17/06 | (2006.01) |
| A61C 5/14 | (2006.01) |
| A61C 19/06 | (2006.01) |

(52) U.S. Cl.
CPC ............ *A61F 5/566* (2013.01); *A61M 25/02* (2013.01); *A61C 17/043* (2013.01); *A61C 5/14* (2013.01); *A61C 19/063* (2013.01)

(58) Field of Classification Search
CPC ..................................................... A61F 5/566
USPC ................. 128/848, 846; 433/93, 91, 25, 140
See application file for complete search history.

(56) References Cited

U.S. PATENT DOCUMENTS

| | | | | |
|---|---|---|---|---|
| 2010/0288288 A1* | 11/2010 | Hegde et al. | ............. | 128/848 |
| 2010/0294283 A1* | 11/2010 | Li | ............. | 128/848 |
| 2012/0024297 A1* | 2/2012 | Hegde et al. | ............. | 128/848 |

* cited by examiner

*Primary Examiner* — Alireza Nia
*Assistant Examiner* — Tarla Patel
(74) *Attorney, Agent, or Firm* — Mark David Torche; Patwrite LLC

(57) ABSTRACT

A device for snoring and obstructive sleep apnea treatment has an oral elastic glove portion adapted to removably cover a free moving portion of a user's tongue. Three vacuum suction cups are used to attach the device to the hard palate and the dorsal and ventral surfaces of the tongue in order to hold the device in place without allowing the tongue to move backwards. A vacuum creating cannula and a syringe attached to a tip of the device to create a vacuum once the device in positioned in the user's mouth. In addition, a balloon is provided to prevent soft palate vibrations. A skin attachment pad is removably attached to the user's face close to the mouth and holds the end of a string provided to secure the tongue glove from moving during sleep or be accidentally swallowed.

6 Claims, 10 Drawing Sheets

DEVICE FOR SNORING AND OBSTRUCTIVE SLEEP APNEA TREATMENT

BACKGROUND OF THE INVENTION

The tongue and soft palate play a major role in production of snoring and obstructive sleep apnea. Without their participation, these symptoms could not be present. Hence, it is imperative to have knowledge about these structures, which play an important role in snoring and obstructive sleep apnea, to understand our invention. The tongue is a muscular organ, without bones, and richly supplied with nerves and blood vessels (FIG. 3a). The tongue also serves as a natural means of cleaning one's teeth by its multi-directional movement capability. It is kept moist by saliva and mucous glands of the oral cavity.

The average length of the adult human tongue is 10 cm (4.5 inches) from the oropharynx to the tip. It is divided by a V-shaped shallow groove called the sulcus terminalis, into an anterior two thirds and a posterior one third with the foramen cecum (FIG. 1) in the center of the angle. The tongue is lined by thick stratified squamous epithelium which continues with the rest of the oral mucosa. This mucosal covering the upper surface of the tongue is thrown into several projections called the lingual papillae in the anterior two thirds of the tongue. These papillae give the roughness to the dorsal surface of the tongue and helps hold our inventive device, firmly. In the posterior one third, there are no papillae; but, there are numerous discrete masses of lymphoid follicles projections called lingual tonsils.

There are three types of papillae: fungiform (mushroom like), filiform (thread like), circumvallate papillae (cup and saucer shaped) and foliate papillae (rare in humans). Underneath the papillae, there are mucous and serous glands, pockets of adipose tissue, a layer of skeletal muscle and connective tissue. Many of these papillae have taste buds which carry taste sensations to the CNS. Von Ebner's glands (also called gustatory glands) are located around circumvallate and foliate papillae in the tongue. They secrete lingual lipase digestive enzyme which flushes particulate from the moat to enable the taste buds to respond rapidly to fresh ingested food and the taste of drinks. The secretions of these glands also inhibit the growth of bacteria.

The tongue is made up of five intrinsic muscles: superior, inferior, longitudinal, transverse, and vertical muscles not attached to any bone, and four extrinsic muscles: genio, hyo, stylo, and palato glossus muscles that are attached to bones (FIG. 3a). The skeletal muscles in the tongue arranged in three different planes. This allows the tongue to perform a number of complex movements in every direction. While asleep in the supine position, all the tongue muscles relax; the muscle mass of the tongue moves back due to weight and gravitational pull resulting in obstruction of the air way causing snoring and obstructive sleep apnea (FIGS. 1, 2, 3).

The palate is located on the roof of the mouth and is made of boney hard palate and muscular, aponeurotic soft palate (FIG. 4). The flexible skeleton for the soft palate is provided by the aponeurosis of tensor palati muscle. There are five pairs of palatine muscles of the soft palate that are involved in the movement of the palate and uvula which participate in the production of snoring. They are: 1: Tensor palati, 2: Levator palati, 3: Palatopharyngeus from the upper surface, 4: with the uvular muscles within the upper surface, and 5: Palato-glossus from the lower surface. The thin muscles with aponeurosis of the soft palate lose their tone during sleep, lengthen in size, move toward the pharynx and the back of the tongue, and act as a resonating instrument like a drum or thick string reverberating with the passage of air during respiration, resulting in snoring during sleep.

The region of the tongue underneath the tip and blade of the tongue called the sublingual region (206, FIG. 4). Here, the oral mucosa is very thin with a rich plexus of veins (seen by lifting the tongue in a mirror) with openings of the submandibular, sub maxillary, mucous and serous glands. Because of its thin mucosal lining, therapeutic agents are easily and rapidly absorbed and delivered to the systemic circulation. That is why the sublingual region is selected as the route of administration of many therapeutic agents. This is the distinct expedient and efficacious route of administration of nitroglycerin to a patient suffering from an acute attack of chest pain from angina pectoris. If the tablet swallowed, the medication is completely neutralized by the detoxification process of the digestive system enzymes and the liver.

The tongue plays a primary role in the production of obstructive sleep apnea (FIG. 3). The dorsal surface of the tongue is constantly in contact with the hard and soft palate except at the posterior surface, which is inclining, and comes in contact with the epiglottis and oropharynx leading to obstructive sleep apnea. In the present invention, the tongue glove anti-snoring device covers the entire, visible, free tongue surface and will come in contact with the palate when the mouth is closed with breathing occurring through the nose.

The palate forms the roof of the mouth and is made up of two regions: the hard palate in front; the soft palate behind (FIG. 4). The hard palate is formed by the palatine processes of the maxillae. The horizontal plates of the palatine bones behind it continue with the soft palate. It is the soft palate that plays a role in snoring; and it plays a role with the tongue in obstructive sleep apnea. The soft palate is suspended from the posterior border of the hard palate, and extends downwards and backwards between the oral and nasal parts of the pharynx. It consists of mucous membrane enclosing an aponeurosis, muscular fibers, vessels, nerves, lymphoid tissue and mucous glands.

Its superior border is attached to the posterior margin of the hard palate, and its sides are blended with the pharynx. Its inferior border is free, which contributes to snoring. The uvula is a diminutive conical process suspended from the middle of its lower border and has two curved borders of mucous membrane. It contains muscular fibers (palatoglossal arch) and extends laterally and downwards from each side of the base of the uvula. A fibrous lamella, the palatine aponeurosis is attached to the posterior border of the hard palate and to the inferior surface of the hard palate behind the palatine crest which supports the palatine muscles and gives strength to the soft palate. The muscles of the palate (208, FIG. 4) include a levator and a tensor of the palate; the muscles underlying the palatoglossal and palatopharyngeal folds and extending into the palate itself; and the muscle of the uvula. The soft palate plays an important role in snoring. The flexible skeleton for the soft palate is provided by the aponeurosis of tensor palati muscle on which the soft palate moves when relaxed during snoring.

Snoring, hypopnea and obstructive sleep apnea are caused by the vibrating soft palate, the soft tissue of the nasal, oral and laryngeal pharynx; along with the relaxed tongue moving backwards towards the oral and laryngeal pharynx; thus, blocking of the air passageway through the pharynx. Snoring is an inspiratory sound which arises in the course of a person's sleep and is due to the narrowing of the naso-oro- and laryngo-pharyngeal airway and is mostly produced by the soft palate. The sounds of snoring are generated by vibration of soft tissues of oropharynx which involves the soft palate, uvula, tongue, lips, the posterior faucial pillars of the tonsils, pharyngeal folds, posterior, lateral pharyngeal wall and epiglottis in the upper airway.

Many causes for the narrowing of the nasal pharyngeal airway exist, especially during sleep, besides the flaccid soft palate and the tongue. People who snore rarely make snoring sounds when breathing while awake in the same position that is associated with snoring when asleep (FIGS. 1, 2, 3). The reason being that the wide-awake, conscious person has watchful control over the various muscles of the upper airway so as to prevent the vibrations that cause snoring to occur (FIG. 1). During sleep, the motor neurons that control skeletal muscles are inhibited from sending instructions to make them active and increase the tone of these muscles. This physiological process in sleep results in flaccid muscles that permit soft tissue to sag and collapse into the pharyngeal airway resulting in snoring and obstructive sleep apnea strikes (FIGS. 2, 3).

It has been estimated that up to 45% of all adults snore, sporadically with about 25% being constant snorers. It is known that snoring increases with advancing age and it has been observed that about 50% of men and 40% of women are habitual snorers by the age of 60 (Lugaresi, et al, "Snoring: Pathogenic, Clinical and Therapeutic Aspects", Reported in Principles and Practice of Sleep Medicine (Kryger et al, Editors 1989) at pp. 494-500). With increasing weight gain and epidemic of obesity, the snoring and obstructive sleep apnea is bound to increase.

TYPES OF SLEEP APNEA: There are three types of sleep apnea. They are as follows:

1. Obstructive sleep apnea is the common form of the condition when the tissues of the naso-oro-laryngeal-pharynx obstruct breathing during sleep. These pauses in breathing, called apneas, usually last 20 to 40 seconds. There are more than 20 million people who suffer from obstructive sleep apnea in the U.S., and its occurrence in the adult population is estimated to be 3-4% in women and 6-7% in males. People who gain weight, develop obesity, have craniofacial syndromes (mostly genetic), have repairs of the cleft palate, Down Syndrome, small mandibles, receding chins, etc. have a higher risk of developing obstructive sleep apnea than most individuals. The present invention is intended to treat the conditions causing obstructive sleep apnea.

2. Central sleep apnea is due to neurological condition resulting from a head injury, stroke, various central nervous system disorders, and/or heart failure. Patients with central sleep apnea should avoid using sedatives, narcotics, and alcohol. Treating the primary etiology will, in most cases, eliminate the condition. Unfortunately, the primary etiology may be terminal.

3. Mixed sleep apnea is due to physical oropharyngeal airflow obstruction associated with central (CNS) etiology. It is a rare condition, but is the most dangerous form of sleep apnea and it is difficult to treat. The present invention is provided to treat this form of obstructive sleep apnea, as well.

Symptoms of obstructive sleep apnea are:
frequent cessation of breathing (apnea) during sleep (sleeping spouse or companion may notice repeated silences from your side of the bed
then sudden awakenings to restart breathing with choking or gasping during sleep to get air);
loud snoring;
waking up in a sweat during the night due to lack of oxygen and resulting carbon dioxide build up;
waking up restless in the morning after a night's sleep with or without headaches, sore throat, or dry mouth in the mornings;
daytime sleepiness including falling asleep at improper times, such as during driving, at work, at meetings and conferences; mood changes such as irritability, anxiety and depression; trouble concentrating; forgetfulness reduced and
dwindling sex drive; unexplained weight gain; increased urination and/or nocturia; frequent heartburn, gastro-esophageal reflux disease (GERD); and heavy night sweats.

Studies by Lee, et al. have shown that the oxygen desaturation detected in all patients with obstructive sleep apnea. It is not found in simple snorers (Lee C H, Mo J H, Kim B J, Kong I G, Yoon I Y, Chung S, Kim J H, Kim J W, Arch Otolaryngol Head Neck Surg. Evaluation of soft palate changes using sleep video fluoroscopy in patients with obstructive sleep apnea. 2009 eb; 135(2):168-72). Studies show that the soft palate was considerably elongated and angulated in patients with obstructive sleep apnea, even when awake. Hence, the treatment of snoring should be differentiated for the sake of treatment: 1: to prevent production of sound during sleep, 2: to correct the obstructive sleep apnea with serious health consequences. The present invention is intended for treatment of both conditions.

There are no effective FDA approved drug treatments for obstructive sleep apnea. Nevertheless, a clinical trial of antidepressants mirtazapine (brand names: REMERON, AVANZA, ZISPIN) has shown some hopeful results in the treatment of obstructive sleep apnea. Mirtazapine is not a serotonin uptake inhibitor (SSRI) reuptake inhibitor. It disinhibits dopamine and norepinephrine activity in various parts of the brain, notably in the pleasure centers such as the ventral tegmental area, causing a pronounced antidepressant and anxiolytics response due to the release of the neurotransmitters dopamine and norepinephrine.

SSRIs such as fluoxetine, tryptophan, protriptyline; oral methylxanthine and theophylline (chemically similar to caffeine), amphetamines stimulants; to anti-narcoleptic medications such as modafinil are also tried. A course of anti-inflammatory steroids such as prednisone (or another glucocorticoid drug) is given to reduce the lymphoid tissue of the naso-oropharyngeal air passages if enlargement of the lymphoid tissue is found and the allergic conditions are suspected.

A basic treatment for snoring and obstructive sleep apnea involves having the patient sleep in the prone position or on his/her side. Sometimes this is stimulated by sewing an object into the back of the snorer's clothes. In obese patients, treatment includes weight loss. Along with these treatments, it is recommended that the patient avoid use of CNS depressing drugs, cigarettes, or alcohol prior to bedtime to prevent or reduce the loss of oropharyngeal muscle tone.

Obstruction due to enlarged tonsils or adenoids may indicate the need for their removal. In some cases, surgical repair of a deviated nasal septum has been shown to improve snoring. A reduced pharyngeal passageway may also be caused by a lack of muscle tone. Other anatomical conditions contributing to the narrowing of the nasal, oral, and laryngeal pharyngeal air passageway include choanal atresia, chrono polyp, nasal septal deviation, nasal and pharyngeal cysts, macroglossia, retrognathia, and micrognathia and countless other etiologies. Snoring and obstructive sleep apnea might be aggravated by alcoholic drinks or drugs (such as tranquilizers, hypnotic, sleeping pills, and antihistamines) taken prior to bedtime. Smoking is also held responsible for snoring, since cigarettes may irritate the mucus membranes of the upper airway and oropharynx; causing swelling and increased mucus production. Where snoring is caused by nasal allergy or an upper respiratory tract infection, these conditions may be treated with antiallergenic treatment (Douglas N J "The Sleep Apnoea/Hypopnoea Syndrome And Snoring", British Medical journal, 1993, Vol. 306:1057-60; Leung et al, "The ABZzzz's of Snoring" Post Graduate Medicine (Sep. 1, 1992).

Anti-snoring and anti-obstructive sleep apnea devices abound. Some of them are shown to be effective when they pull or hold the mandible (lower jaw) forward and upward and, elevate the tongue as the muscles of the mandible relax, so that the tongue does not occlude the air passageway drifting, inferiorly and posteriorly while sleeping so as to prevent the passage of air. Some of the devices are just attached to the tip of the tongue with vacuum and held in position by dental bites while asleep. Most anti-snoring devices accomplish this task by moving the lower jaw forward and holding that position against a rigid upper dental component, which is fixed to the upper teeth in the immobile maxilla and to the lower teeth in the mandible.

The disadvantages in using the above prior art devices, is that they require expert, qualified, licensed lab services for fitting of the anti-snoring device to the user's mouth. Such devices could cause permanent irremediable changes in the bite of the user and permanently alter the jaw position, and it requires a dentist to closely monitor the anti-snoring device's fitting. There is a need for an anti-snoring device that does not rigidly bind to the dental structures of the user's mouth and that does not require professional supervision or assistance in its fabrication, monitoring of the dental bite changes and mandibular changes. In addition, the anti-snoring device should not pit the lower jaw against the upper jaw. These devices do not include an intra-oral dental overlay to support the tongue against the palate and keep the palate of the user's mouth from reverberating (snoring) during mouth breathing. Our invention overcomes these draw backs.

Snoring and obstructive sleep apnea is also be managed by the use of a positive pressure generator and facemask. In this procedure, a mask covers the nose and mouth or just nose or mouth is used and it delivers air under pressure. The standard method is known as "Continuous Positive Airway Pressure" (CPAP) treatment, which requires the patient wear a mask through which air is blown into the nostrils in order to keep the airway open. Patient compliance is poor due to discomfort and side effects. CPAP pneumatically splints the upper airway. Use of this devices cause the subject to become non-compliant due to the difficulty in its use due to discomfort during sleep. Problems that may occur with CPAP include: restless sleep, dryness of nose, throat, nasopharyngeal tract, cough, excessive dreaming during early use, nasal congestion, runny nose, sneezing, irritation of the eyes and the skin on the face, abdominal bloating, and leaks around the mask because it does not fit properly.

The person may be able to limit or stop some of the side effects; the doctor may be able to adjust one's CPAP to reduce or eliminate problems and make sure the mask or nasal prongs fit properly (air should not leak around the mask); and/or the patient may use a humidifier or a corticosteroid nasal spray medicine to reduce nasal congestion, irritation, and drainage.

Users of this method of treatment may need to talk to a doctor about trying a CPAP machine that will help to reduce discomfort caused by too much constant pressure in the user's nose. If this does not improve discomfort, ask your physician about trying a bi-level positive airway pressure machine (Bi-PAP-VPAP or variable positive airway pressure) which uses a different air pressure when you breathe in than when you breathe out. BiPAP may work better than standard CPAP for treating obstructive sleep apnea in people who have heart failure. Almost every patient of snoring and obstructive sleep apnea dislikes using this bulky cumbersome, bothersome equipment; hence, compliance is low.

A more recent treatment option for obstructive sleep apnea includes the implantation of rigid inserts in the soft palate to provide structural support; it is both invasive and is only effective for mild to moderate cases of obstructive sleep apnea. Alternative treatments are even more invasive and drastic including tracheotomy, genioglossus advancement or stimulator, hyoid suspension, tongue reposition, and tissue ablation (somnoplasty or uvulopalatopharyngoplasty.

If all else fails, sleep apnea treated by maxillomandibular advancement where lower part of patients face is moved forward approximately 12 millimeters; reduction of the size of the soft palate; laser-assisted uvulopalatoplasty; and/or reduction of the tongue base either with laser excision or radiofrequency ablation or by hyoid bone suspension in the neck. In rare intractable cases, a tracheotomy is the only effective last resort treatment for sleep apnea.

Due to many associated disadvantages, complications and high failure rate, these tissue ablation methods and radical surgeries need to be considered as a last resort. Surgical removal of the uvula, distal portion of the soft palate, the anterior tonsillar pillars, adenoids, tonsils and the redundant lateral pharyngeal wall mucosa is said to increase the size of the air passageway allowing unobstructed movement of air through the pharynx during sleep. Rates of success of the uvulopalatopharyngoplasty are reported to be in a range from 15% to 65%. (Douglas, "The Sleep Apnoea/Hypopnoea Syndrome And Snoring", British Medical journal, 1993, Vol. 306:1057-60).

Obstructive sleep apnea causes high blood pressure, depression, irregular heartbeats, heart failure, coronary artery disease, and stroke. If the person is overweight, bariatric surgery may help with weight loss, which may improve snoring and sleep apnea.

U.S. Pat. No. 5,569,679 discloses the use of nasal solution 10%-16% of methylsulfonylmethane (MSM) drops for the treatment of anti-snoring method. It is a nasal spray, too simplistic to treat complicated anatomically related snoring with or without obstructive sleep apnea whose pathophysiology is rarely in the nose.

U.S. Pat. No. 5,921,241 discloses an anti-snoring device including a moldable dental overlay for covering the lower teeth of the user and for maintaining the tongue in contact with the palate to prevent air flow from causing the palate to reverberate during mouth breathing.

U.S. Patent Application Publication Number: US 2004/0153127 A1 invention provides electrical stimulation that causes the oropharyngeal muscles to contract during sleep using one or more micro stimulators injected into or near these muscles or the nerves which innervate them.

U.S. Patent Application Publication Number: US 2007/0233276 A1 describes the method and apparatus that includes placing a tissue contractor within the tongue tissue. This is an invasive procedure and may create discomfort and complication after surgery.

U.S. Pat. No. 6,418,933 B1 discloses an anti-snoring device that has maxillary and mandibular bite forms with outwardly extending pivots which are mounted to the bite forms by frameworks which are at least partially embedded in the bite forms.

U.S. Pat. No. 5,499,633 shows two bite forms which may be joined so that the user's mandible projects forwardly of its normal position in order to reduce snoring.

U.S. Patent Application Publication Number: 2005/0178392 A1 discloses a small piece of cloth tape or other porous hypo allergenic material with a hypo allergenic adhesive on the back that is affixed to the lips before sleeping. This may not be effective in preventing the vibration of the soft palate and snoring with or without obstructive sleep apnea.

U.S. Pat. No. 7,016,736 B2 discloses a submental electrical stimulation of the supra hyoid muscles at the floor of the mouth, but does not address the snoring due to vibration of the soft palate and uvula.

Numerous management techniques have been described, and none of these treatments have proved adequate; most of the therapies are inadequate to treat snoring and obstructive sleep apnea and cumbersome to use. Surgery for the condition is filled with fear and complications besides the high cost and high rate of failure. Hence, the snoring with or without obstructive sleep apnea remains a serious slow evolving health problem. With increasing obesity, snoring and obstructive sleep apnea is increasing in the general population along with type II diabetes. Accordingly, there has been a need for improved management techniques to reduce or eliminate snoring and obstructive sleep apnea by using simple and safe methods. The devices in the present invention designed to be used to treat snoring and obstructive sleep apnea with minimal or no complications, having the least disadvantages, being affordable, and having the highest compliance.

SUMMARY OF THE INVENTION

A device for snoring and obstructive sleep apnea treatment has an oral elastic glove portion adapted to removably cover a free moving portion of a user's tongue. Three vacuum suction cups are used to attach the device to the hard palate and the dorsal and ventral surfaces of the tongue in order to hold the device in place without allowing the tongue to move backwards. A vacuum creating cannula and a syringe attached to a tip of the device to create a vacuum once the device in positioned in the user's mouth. In addition, a balloon is provided to prevent soft palate vibrations. A skin attachment pad is removably attached to the user's face close to the mouth and holds the end of a string provided to secure the tongue glove from moving during sleep or be accidentally swallowed.

Other features and advantages of the instant invention will become apparent from the following description of the invention which refers to the accompanying drawings.

DETAILED DESCRIPTION OF THE INVENTION

Figure 1:
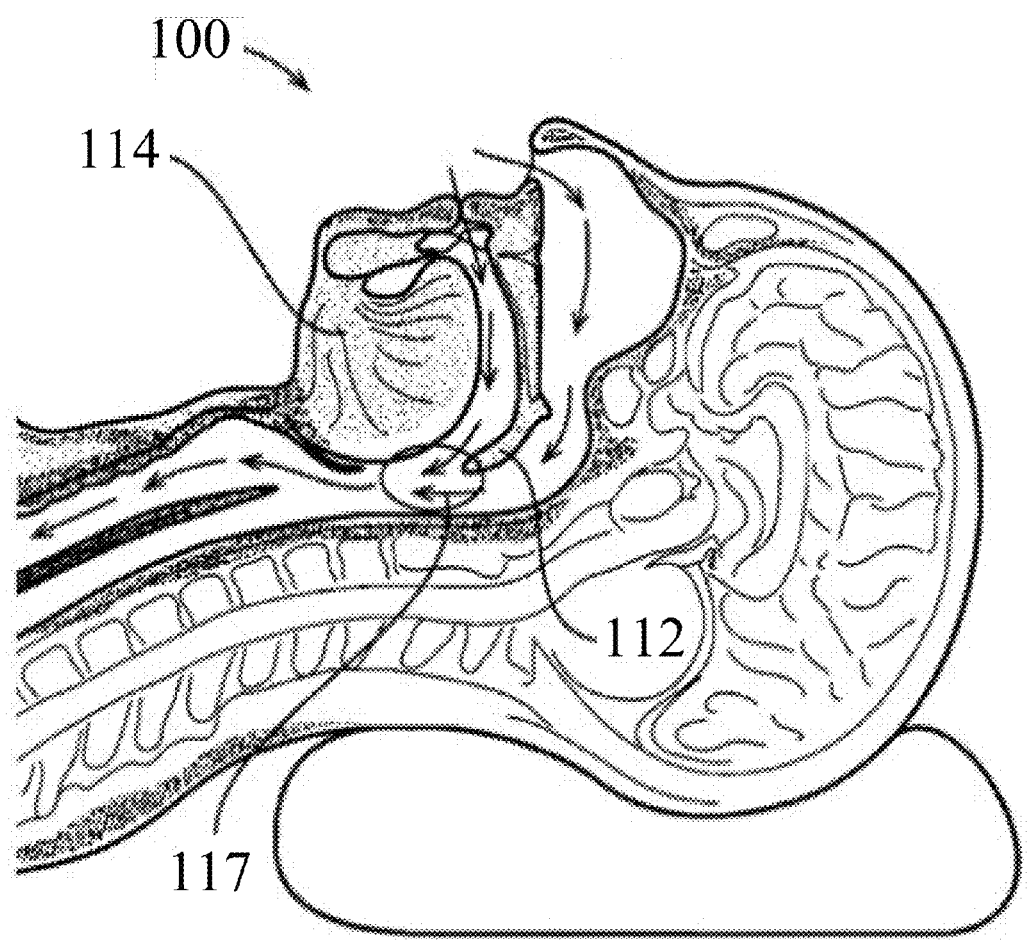
FIG. 1 is a diagrammatic presentation 100 of the air way during awake and sleeping without snoring.

In the following detailed description of the invention, reference is made to the drawings in which reference numerals refer to like elements, and which are intended to show by way of illustration specific embodiments in which the invention may be practiced. It is understood that other embodiments may be utilized and that structural changes may be made without departing from the scope and spirit of the invention.

According to the present invention, snoring and obstructive sleep apnea patients is treated by recognizing patient condition attributable at least in part to the vibration of the soft palate during inspiration and movement of a base of a tongue of said patient moving towards a pharyngeal wall of said patient to cause obstructive sleep apnea. The present invention prevents the tongue of the patient from obstructing the air passage so as to cause snoring and obstructive sleep apnea.

FIG. 1 is the diagrammatic presentation of the normal air way 100 with the soft palate 112 and tongue 114 not obstructing the airway passage 117 allowing the free flow of air from the mouth and the nose to larynx as the person sleeps on a pillow in a supine position. The airflow does not produce a physical force like a narrow air stream; hence, neither snoring, nor obstructive sleep apnea produced.

Figure 2:
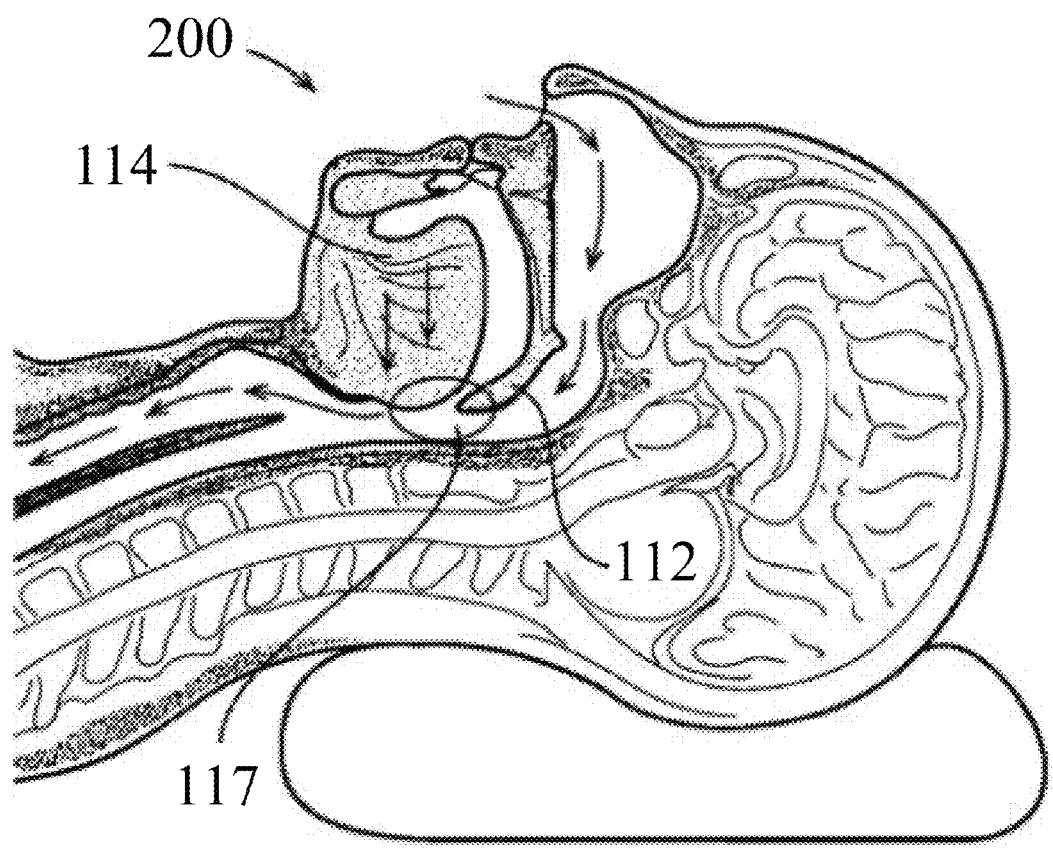
FIG. 2 is a diagrammatic presentation of the airway 200 with soft palate 112 and tongue 114 partially obstructing the airway resulting in snoring

FIG. 2 is the diagrammatic presentation of the air way 200 with the soft palate 112 and tongue 114 partially obstructing the airway 117 not allowing the free flow of air from the mouth and the nose as the person sleeps. The air flows in a narrow stream through the air passages 117 vibrating the soft palate 112 and soft tissue around the tongue 114 producing snoring as one sleeps. This is due to relaxation of the soft palate 112 and tongue 114 becoming flaccid and falling back so as to create forcible air stream like venturi wind tunnel effect, especially the soft palate 112, which comes in contact with narrow stream force of air so as to produce sound as one falls asleep. The present invention prevents the soft palate and tongue coming in contact and thus prevents snoring and sleep apnea.

Figure 3:
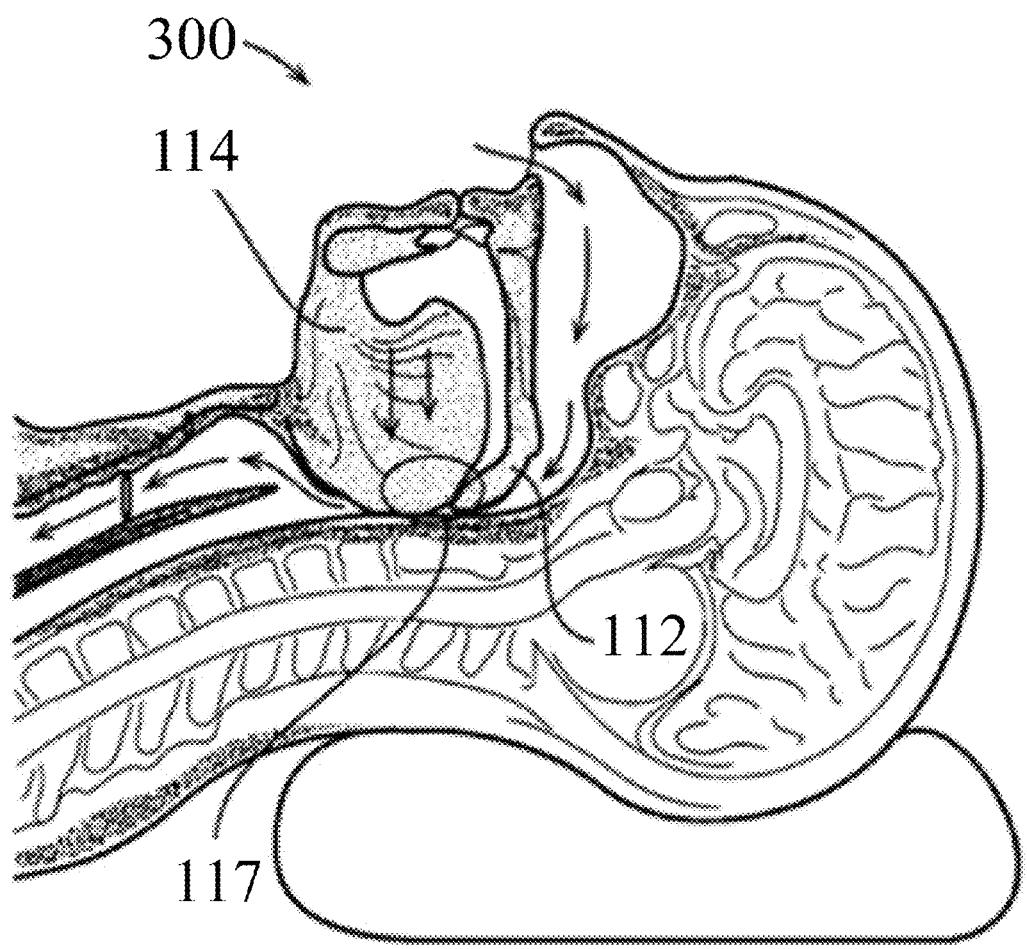
FIG. 3 is a diagrammatic presentation of the airway 300 with soft palate 112 and tongue 114 completely obstructing the airway resulting in obstructive sleep apnea.

FIG. 3 is the diagrammatic presentation of the airway 300 with the soft palate 112, tongue 114 completely obstructing the airway 117 by not allowing the free flow of air from the mouth, and the nose to the larynx, through the oropharyngeal air passageway to the laryngeal inlet as a person sleeps. This is due to relaxation of the soft palate 112 and the tongue 114 becoming flaccid and falling back due to reduced skeletal muscle tone on the wall of the oropharynx 117 creating obstruction to passage of air resulting in snoring and obstructive sleep apnea. Due to this physical blockage by the tongue, the person becomes aware of the obstruction due to central nervous system activation by carbon dioxide build up in the blood. This results in the partial opening of the airway allowing the air stream which causes the vibration of the soft tissue of the oropharynx, especially the soft palate 112, which comes in contact with narrow stream force of air so as to produce snoring sound as one falls asleep. The narrow stream of air flow or complete obstruction to air passage 117 results in vibrating the soft palate 112, and the soft tissue around the tongue 114 producing snoring and complete obstructive sleep apnea (OSA). The present invention prevents such movement of the palate and tongue to cause obstructive sleep apnea and allow the air to pass to the larynx.

Figure 3A:
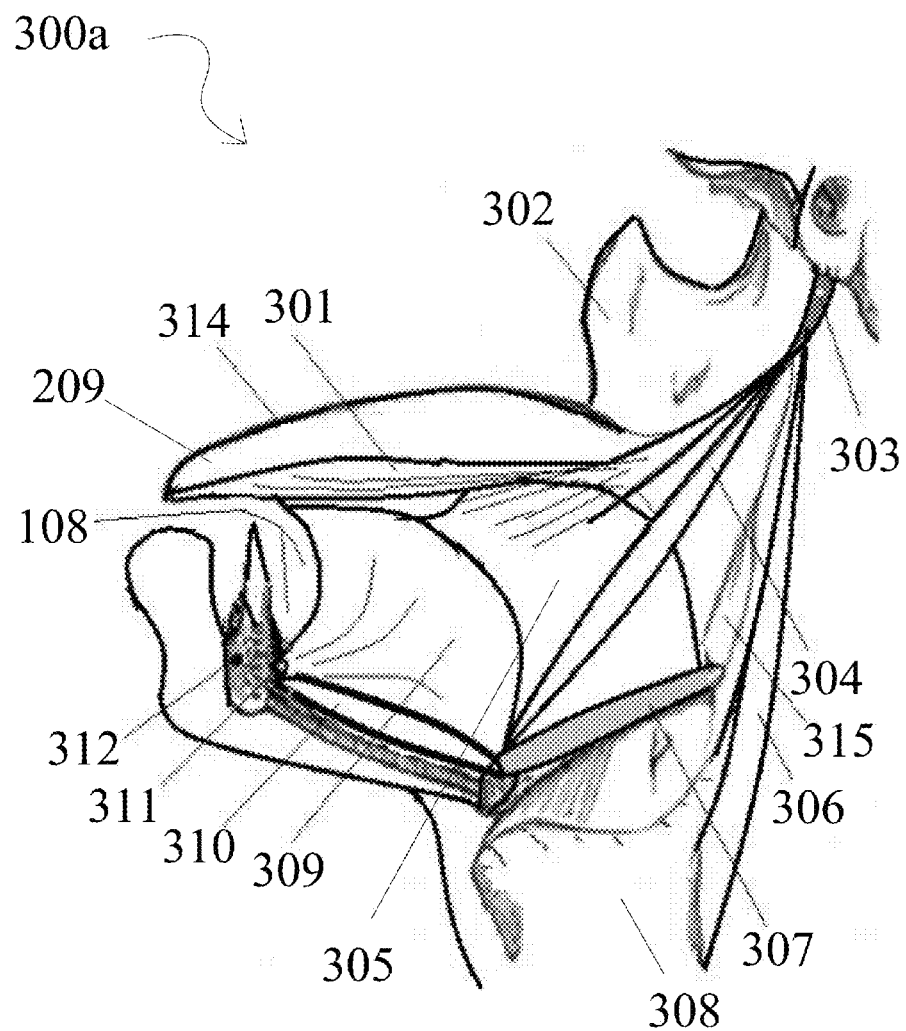
FIG. 3a is a diagrammatic presentation 300a showing the muscles involved in the movement of the tongue and obstructive sleep apnea.

FIG. 3a is the diagrammatic presentation 300a showing the muscles involved in the movement of the tongue 209 and obstructive sleep apnea. It shows Stylo-golssus muscle 301, Ramus of the Mandible 302, Styloid processes 303, Stylohyoid muscle 304, Hyo glossus muscle 305, Stylo thyroid muscle 306 with stylo hyoid ligament 315 behind it attached to the posterior end of the hyoid bone 307, Thyroid cartilage 308, Genio glossus muscle 309, Genio hyoid muscle 310, Genoid tubercle 311, and Mandible 312. Maintaining proper tone of these muscles is responsible for prevention of the OSA during sleep. A dorsal surface 314 of the tongue 209 with intrinsic muscles without any bony attachment moves en-mass backwards and downwards towards the oral and laryngeal pharynx and is responsible for the obstruction of the airway resulting in OSA (see FIGS. 3 and 4) when these muscles loose tone during sleep. Though all the muscles shown in the diagram including suprahyoid and infrahyoid play a role in obstructive sleep apnea, the genioglossus 309 plays a major role in the obstructive sleep apnea when it is relaxed. It allows the tongue 209 to move backwards during sleep. The present invention prevents the movement of the tongue due to relaxation of the tongue muscles that produce OSA. The sublingual region (under surface) 108 of the tongue is lined by a very thin layer of mucosal cells. The Sublingual region 108 also acts as site for transmucosal delivery of diverse therapeutic agents due to its physiological effect as a site for rapid absorption of certain therapeutic agents such as insulin, nitroglycerine, vitamins, hormones etc. and provides a space for placement of electrical stimulator to increase the tone of the suprahyoid muscles of the root of the tongue.

Figure 4:
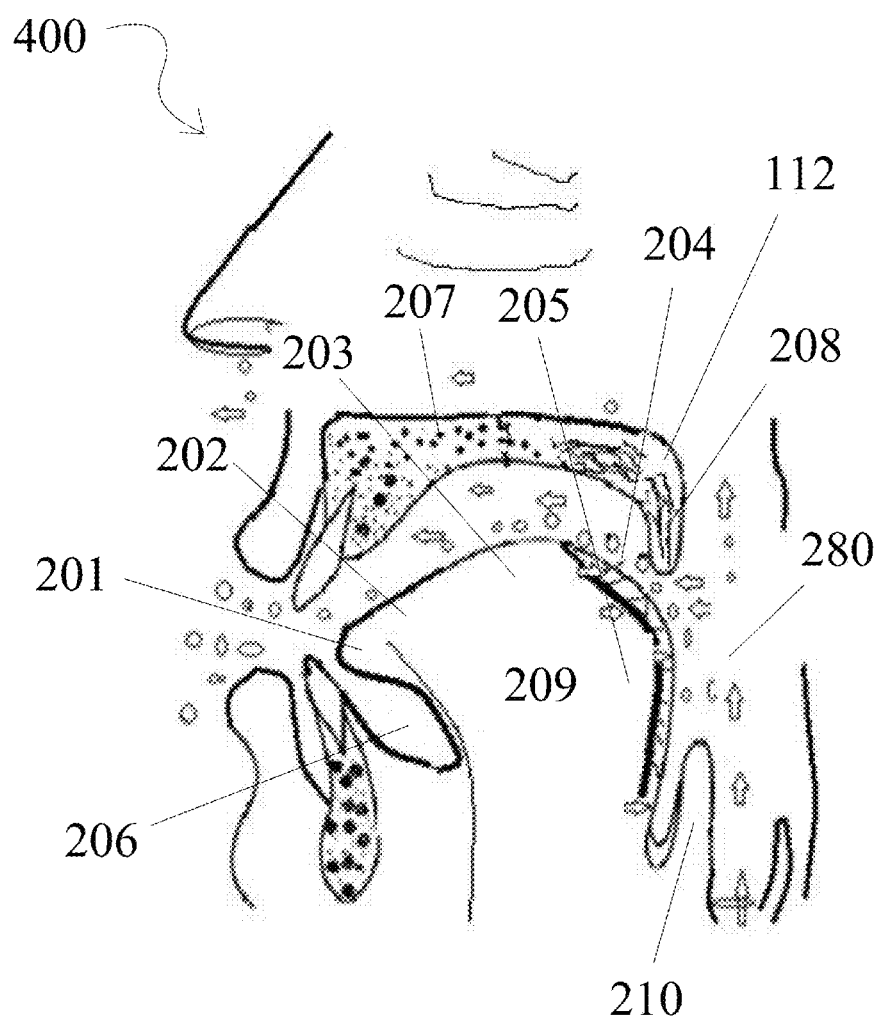
FIG. 4 is a view of the diagram 400 showing various anatomical regions of the tongue, on which the present inventive device is placed to prevent snoring and obstructive sleep apnea

FIG. 4 is a diagrammatic presentation 400 of various anatomical regions of the tongue 209 on which the present device for snoring and obstructive sleep apnea treatment is placed to prevent snoring and obstructive sleep apnea. The tongue 209 is labeled from front to back as tip 201, blade 202, front part 203, back 204, and root of the tongue 205. It also shows the region of the tongue 209 which comes in contact with the oral pharynx 280 to produce obstructive sleep apnea and the zone of the tongue 209 which produces most of the bad breath (halitosis). The dorsal surface of the tongue 201, 202, 203 comes in contact with the hard palate 207 to which the vacuum cups of the present invention are attached firmly and the soft palate with uvula 208 elevated by a balloon to prevent snoring (see FIGS. 5-7). Uvula 208 is adjacent to soft palate 112. Note: the tongue root 205 is close to the proximity of the epiglottis 210 which moves back to obstruct the air passage during obstructive sleep apnea. The tip 201 and blade 202 under the lower surface (sublingual region) 206 of the tongue 209 is lined by a very thin layer of mucosal cells with rich blood vessels, sub mandibular, sub maxillary, and sub mucosal glands openings. Many therapeutic agents (e.g. vitamins, nitroglycerine, hormones, micro therapeutic agents, etc.) are delivered through this region which are rapidly absorbed and delivered to the systemic circulation for immediate effects (e.g., angina pectoris). The present invention is attached with vacuum and vacuum cups enclosing the tip 201, blade 202, and front part 203 of the tongue to prevent snoring and obstructive sleep apnea as shown in the FIG. 8.

Figure 5:
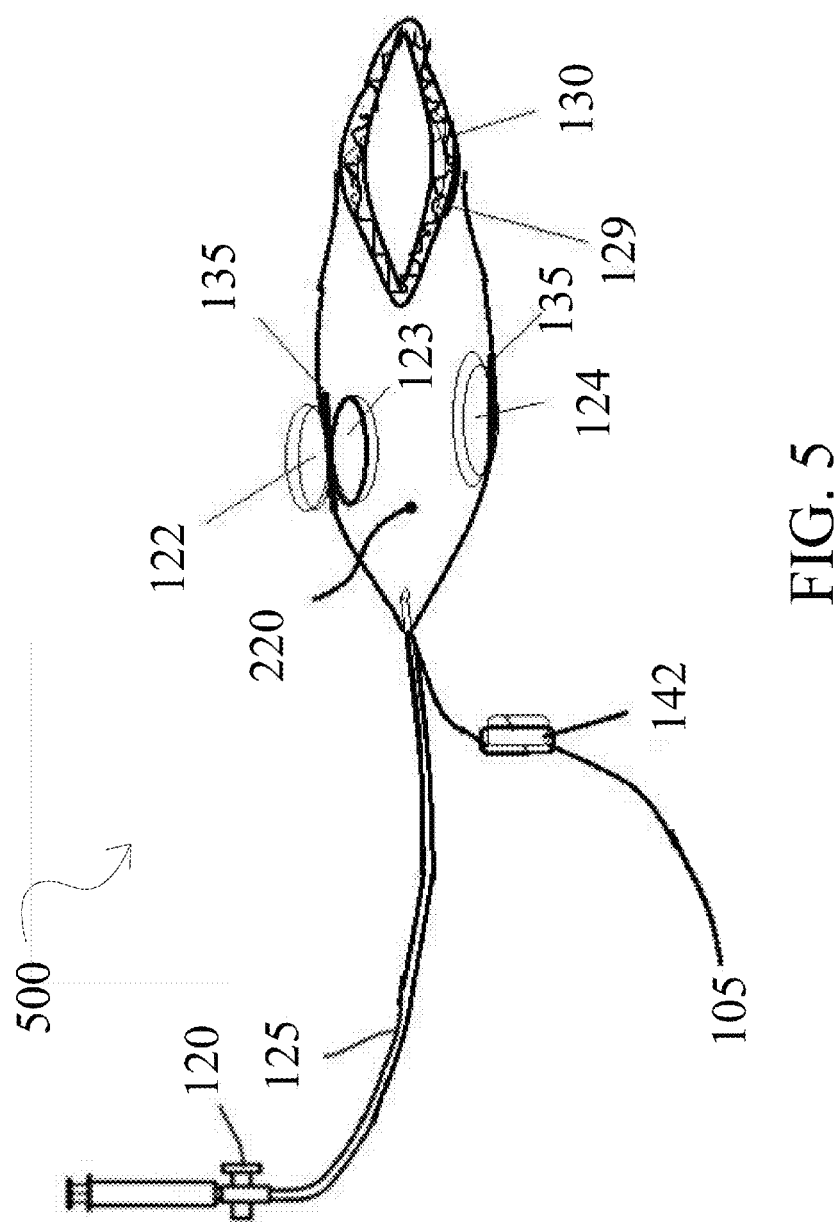
FIG. 5 is a side view of the diagram 500 showing the device used for stopping snoring and obstructive sleep apnea.
Figure 8:
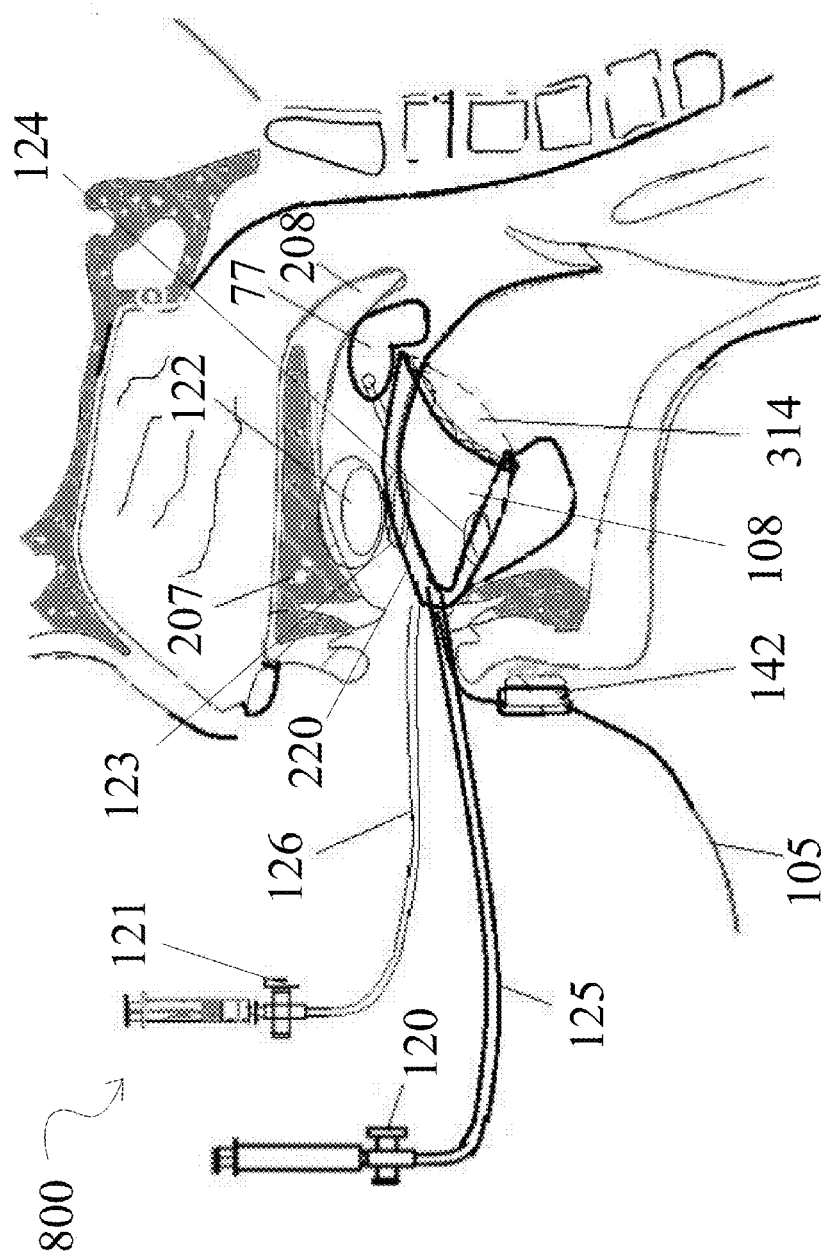
FIG. 8 is a view of the diagram 800 showing one of the embodiments used for stopping snoring and obstructive sleep apnea device in position.

FIG. 5 is a diagrammatic presentation of a tongue glove anti-snoring and anti-sleep apnea device 500 showing a glove portion 220 that covers tip 201, blade 202 and front part 203 and used to treat snoring and obstructive sleep apnea. Referring to FIGS. 4, 5 and 8, the device 220 is made of elastic plastic, synthetic, semi synthetic material or any other material suitable to comfortably cover the selected portion of tongue 209. Glove portion 220 is shaped like the anterior two thirds of the tongue 209 and slides easily over tip 201, blade 202 and front part 203 of the tongue 209. It has an elliptical fish mouth shaped opening 130 with elastic ring 129 which slides easily on the free moving tongue and holds the device firmly on the tongue 209. It has a thick plastic plate (or a thin sheet of aluminum plate) 135 on the dorsal and ventral surfaces of the tongue glove device 220 to which vacuum cups 122, 123, and 124 are attached. Plate 135 is used to provide a stable support for suction cups 122, 123 and 124, but it is possible to use device 220 without them. The vacuum cup 122 removably suctions to the hard palate 207, vacuum cup 123 attaches to a dorsal surface of the blade of the tongue 202, and vacuum cup 124 attaches to the lower surface 206 of the tongue.

When suction cups 122, 123 and 124 are attached properly and a vacuum is created, they hold the tongue 209 in position without allowing it to move backwards. Further, a suction tubing portion 125 works in concert with suction creating syringe 120 attached to a tip portion of the tongue glove device 220 to create the vacuum to hold the device attached to front part of the tongue by creating negative suction force due to removal of the air between the tongue and the device by external syringe 120.

Figure 9:
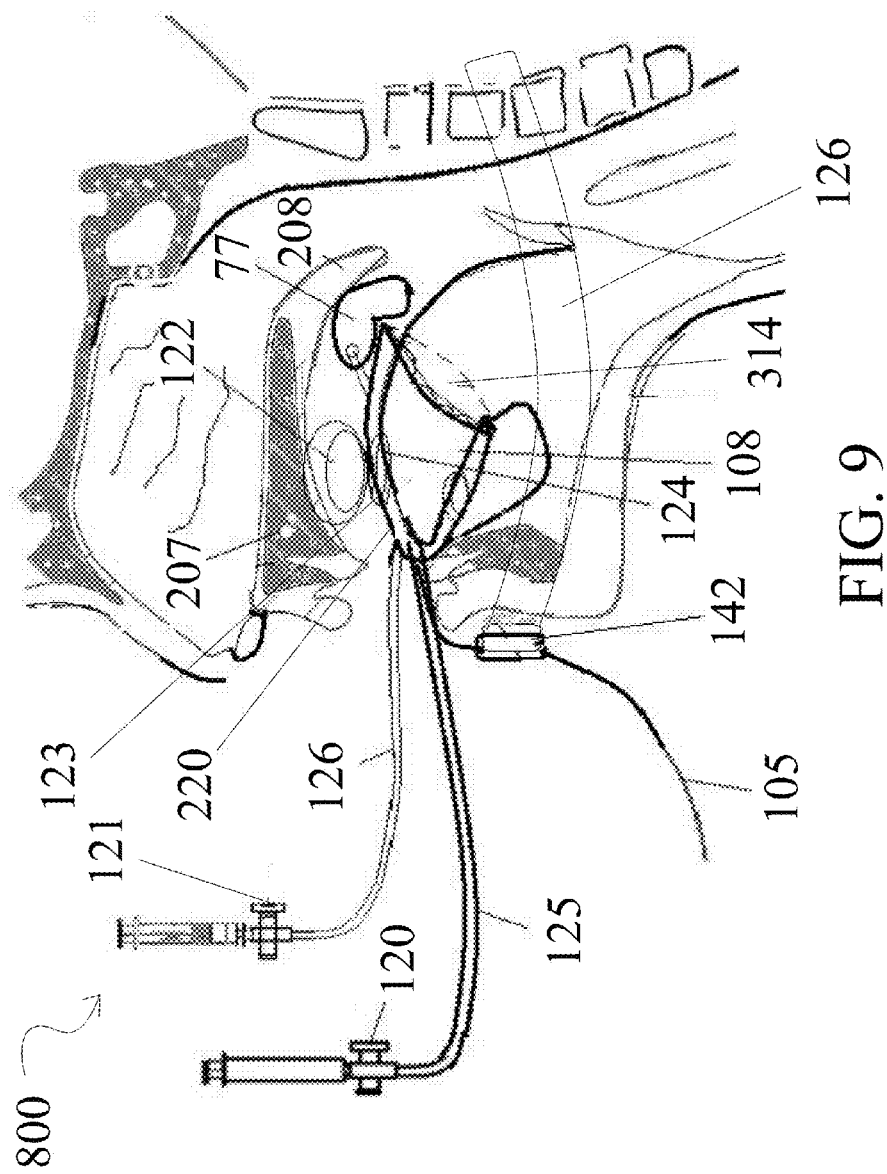
FIG. 9 is a view of the device shown in FIG. 8 with an attachment band.

Referring to FIGS. 5 and 9, the tip of tongue glove 220 has a durable non-stretchable thread 105 attached therein. String 105 comes out of the mouth and attaches to the lower or upper skin attachment pad 142 to prevent the tongue 209 from moving back as one falls asleep, and thus prevents snoring and obstructive sleep apnea and also prevent accidental swallowing or aspiration into the respiratory tract and food passages of string 105. Skin attachment pad 142 either has an matching hook and loop fastening portion or an adhesive to removably secure string 105 to stabilizes tongue glove 220 and does not allow it to move backwards during use. Skin fastener 142 may be applied to the skin using a non-toxic adhesive or attached using a band 126 that removably attaches around the user's chin and wraps around the back of the head to removably secure skin fastener 142. Band 126 may also use a hook and loop fastener or may be made of an elastic material.

Figure 6:
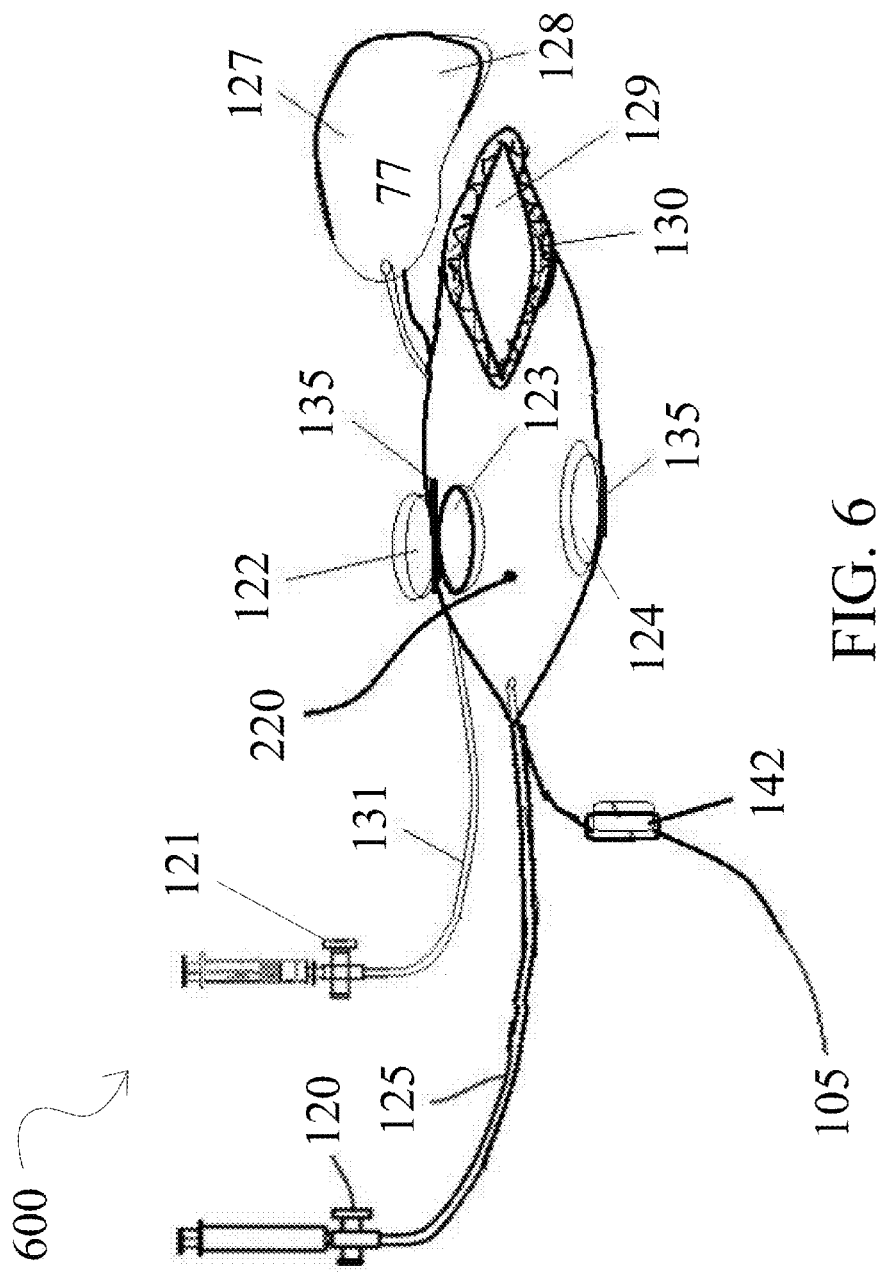
FIG. 6 is a view of the diagram 600 showing the device with balloon used during sleep to stop snoring and sleep apnea, placed in the mouth.

FIG. 6 is a diagrammatic view of the anti-snoring and anti-sleep apnea device 600 showing tongue glove 220 used for the treatment of snoring and obstructive sleep apnea. Referring to FIGS. 1-4 and 6, device 600 has all the components of FIG. 5. In addition, device 600 has a balloon 77 attached to the dorsal surface of tongue glove 220. Balloon 77 has a dorsally placed palatine bulge 127 to hold the hard palate 207 and uvula 208 up and prevent them from coming in contact with the tongue 209. Balloon 77 has a ventral bulge 128 that abuts against the posterior surface of the root of tongue 205 and prevents the tongue 209 from moving back which causes obstruction that causes sleep apnea. Balloon 77 is inflated from outside by using catheter 131 attached to second syringe 121. When inflated with air, gel or liquids, it is expanded and assumes a soft triangular shape that pushes soft palate 112 upwards to prevent it from encountering the dorsal surface of the tongue. It also has a tongue bulge 128, which abuts against the back and dorsal aspects of the tongue 209 and prevents tongue 209 from moving backwards when relaxed during sleep so that there is no development of obstructive sleep apnea during sleep due to blockage of the airway. This device 600 is used both as anti-snoring and anti-obstructive sleep apnea device. The palatine bulge 127 prevents snoring and the tongue bulge 128 prevents the tongue from moving backwards. Again as discussed above, string 105 secures both tongue glove 220 as well as balloon 77 to the lower or upper lip outside the mouth on the skin with adhesive or hook and loop fastener 142 to prevent 220 device from being accidentally swallowed or aspirated into the respiratory tract and food passages. String 105 also prevents tongue 209 from moving backwards during sleep.

Figure 7:
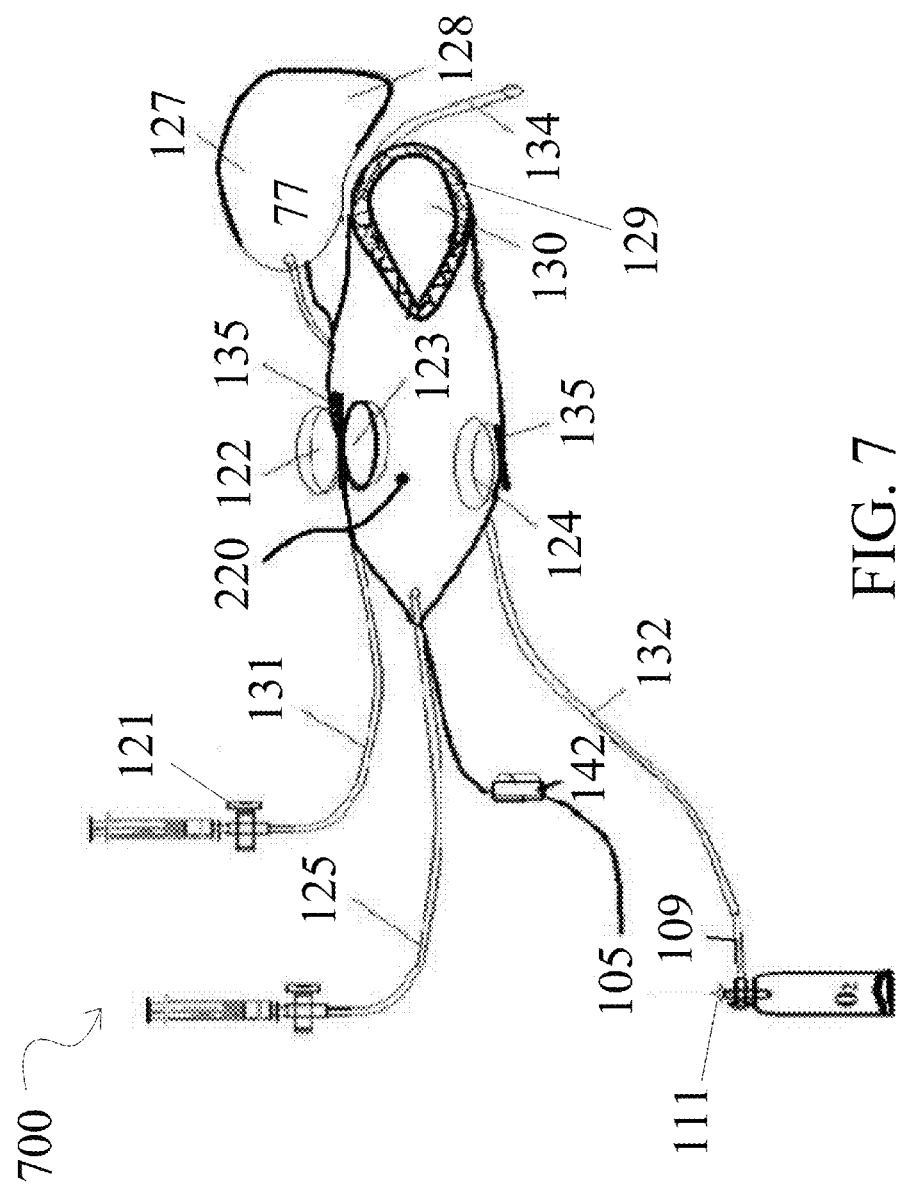
FIG. 7 is a view of the diagram 700 showing the device to stop snoring and obstructive sleep apnea with suctions cups attaching the device to the tongue with cannula to deliver supplemental oxygen.

FIG. 7 is a diagrammatic view of the anti-snoring and anti-sleep apnea device 700 showing tongue glove 220 used for the treatment of snoring and obstructive sleep apnea. Referring to FIGS. 1-7, device 700 has all the components of FIG. 6. In addition, it has provision to transport supplemental oxygen from tank 111 or from oxygen generator (not shown but known in the art), connected through oxygen delivery connector 109 delivered through oxygen delivery catheter 132 with an exit opening close to the laryngeal opening 134 in respiratory compromised patients. It also has a string 105 at the tip of the device to be attached to the lips 142 with an adhesive or hook and loop fastener 142 outside on the skin to prevent accidental swallowing or aspiration of the device into the respiratory tract and food passages as discussed above.

FIG. 8 is a diagrammatic view of the anti-snoring and anti-sleep apnea device 800 showing tongue glove 220 used for the treatment of snoring and obstructive sleep apnea. Tongue glove 220 is shown inside the oral cavity on slipped over the tongue 209 of a user before going to sleep with balloon 77 inflated. The tongue glove 220 is positioned at the free moving anterior part of the tongue 314, covering the undersurface of the tongue 108. Once positioned, the balloon 77 is inflated to abut against the soft palate 112 and uvula 208. Then the free moving part of the tongue 209 is pressed against hard palate 207 to create a vacuum in the concave depression of the suction cups 122 and 123 so that the tongue 209 is held firmly in place. The string 105 is gently pulled until the tongue 209 is moved forward and then attached to the skin on the lips to prevent the tongue 209 from moving backwards. The second syringe 121 with tubing 131 used to deliver air or liquid to inflate the balloon 77 to an appropriate size to lift the soft palate 112 and uvula 208 away from the tongue 209 and prevent the movement of the tongue 209 backwards. The syringe 120 and the tubing 125 attached to the tip of the device is used to suction the air between the tongue and interior surface of the device 220 to hold the tongue in position on the device and held by the string 105 attached externally on the skin surface of the lips as discussed above.

Additionally, a bite block (not shown in the diagram) may be used with the present invention. The bite block (when used) is placed between the incisor teeth in a "V" shaped groove on the bite block. The bite block has incisor teeth sockets located on the bite block for moving the lower jaw forwards on the fixed upper jaw. A planer (lip restrainer) is located outer surface with a perforation to allow the position the palate and tongue bite block with anti-snoring and anti-obstructive sleep apnea device in a proper position with maximum comfort to the user. This bite block planer (lip restrainer) held in proper position with elastic and hook and loop fastener bound around the head; through a hole in the planer surface (lip restrainer) which also allows supplemental oxygen and therapeutic agent's delivery catheters. The tethering string 105 of tongue glove-anti snoring and anti-sleep apnea device described in FIGS. 5, 6, 6, and 8 can pass through between the bite block perforation so as pull the tongue forwards and attach it to the skin on the lips to prevent the tongue from moving backwards.

The present invention, as shown in the FIGS. 5-8, prevents the obstruction to air flow, prevent the palate-uvula-soft tissue vibrating (snoring), and tongue falling back as described (obstructive sleep apnea) in the diagrams by keeping the air way open mechanically; thus, providing the effective method for the prevention and treatment of snoring and obstructive sleep apnea.

The user may soak the tongue glove 220 in an antiseptic solution before use and coat it with lubricant, if needed, (use a lubricant which is not toxic, non-reacting and may be flavored with mint or sweet taste). The interior of the device 220 may be coated with appropriate therapeutic agents to treat any pathological conditions of the tongue. If the device is not tolerable, due to sensitivity, the patient may use local anesthetic lozenges which are available over the counter. If the patient still finds it difficult to use the device due to sensitivity of the oropharyngeal passages, a physician may prescribe a local anesthetic jelly or spray (i.e. CITANEST® spray). The patient should wait until the local anesthetic takes effect; then position it in the mouth on the tongue. If a local anesthetic spray is used, avoid eating food until the numbing effect wears off.

Use a well-lighted mirror to position the tongue glove 220 on the tongue to assure the balloon 77 and tongue bulge 128 are placed appropriately in the correct position and is in contact with the oral undersurface of the hard palate 207, soft palate 112 with uvula 208. Make sure the front end of the tongue glove 220 is attached to the lower or upper lip skin with string 105 provided so that it won't be accidentally swallowed or aspirated while sleeping. Once, the user gets used to employing the device, after a week or two, the user may not need any more topical numbing medications. When not in use, keep the device clean, immersed in antiseptic mouthwash and wash before use in clean, warm water. If oxygen supplementation is needed due any number of lung diseases, use an oxygen concentrator or 100% oxygen from the cylinder 111 and keep the flow to the minimum required levels so that it does not disturb sleep.

Insert the device, to prevent snoring and to prevent snoring associated with obstructive sleep apnea. The user needs to insert the tongue glove 220 to cover all the way back of the tongue 204 starting from the tip 201 and sliding it all the way back to the junction of the front part 203 and back part 204 of the tongue. The device distance on the tongue 204 is adjusted according to the tolerability and convenience of the user. For snoring with obstructive sleep apnea, the balloon 77 is carefully positioned below the soft palate on the tongue, and inflated with air or liquid to the desired comfortable size so as to prevent the tendency of the flaccid tongue falling or moving posteriorly and inferiorly and at the same time balloon 77 lifts the soft palate 112 and uvula 208 away from the tongue 209. After inserting the tongue glove 220 over the tongue 209, press the device against the hard palate 207 with the tongue 209, ensuring suction cups 122, 123 and 124 to hold the device in position on the tongue 209 and tethered to the lower surface 206 of the hard palate 207 and the tongue. Dental adhesives can also be used on the suction cups 122, 123 and 124 to hold the tongue and the tongue glove 220 in position. After the tongue glove 220 firmly tethered on to the tongue 209, then using the suction syringe 125 to create vacuum around the tongue 209 by withdrawing the air between the tongue and tongue glove 209. This method will hold the tongue in a set anatomical position and prevent it moving backwards which can cause snoring and obstructive sleep apnea. Once the correct position is established, pull the anchor string 105 tightly (light tension) and anchor to the upper or lower lips. Then go to sleep without disturbances in the room. If the person is suffering from lung diseases needing supplemental oxygen, turn on the oxygen tank or oxygen concentrator 111 to deliver the supplemental oxygen close to the laryngeal inlet between the back of the tongue 204 and epiglottis 210.

The only way to prevent the tongue from falling back from the floor of the mouth is by mechanical obstruction preventing the flaccid tongue from moving backwards during sleep (especially in supine position); thus preventing obstructive sleep apnea. Such a method is provided by the present invention which prevents soft palate vibrating and the tongue from moving backwards during sleep. This device is to be used every day or as desired with ease.

The tongue glove 220 may be made of thermoplastic or elastomeric resin with a metal component such as stainless steel, aluminum, and copper wiring added to strengthen the composite materials and add mobility to the user's mouth. After waking up, gently remove and clean in warm or hot water; immerse in antiseptic solution, and store it an enclosure or tray. Clean the mouth thoroughly with warm water; brush the teeth, and rinse the mouth after removal of the device with antiseptic mouthwash.

Advantages of the Current Anti-Snoring and Anti-Obstructive Sleep Apnea Inventive Device Advantage of the present invention is that it is available for anti-snoring and obstructive sleep apnea therapies having an external and internal oral device to reduce or eliminate snoring and obstructive sleep apnea during sleep.

An added advantage of the present invention is that it provides for an anti-snoring and obstructive sleep apnea device that is easily self-adjustable and does away with the need for professional and laboratory assistance or clinician fabrication.

Another advantage of using this invention is that it has the provision for introducing supplemental oxygen for those who have severe pulmonary diseases needing high concentration of supplemental oxygen to prevent any adverse health effects due to obstructive sleep apnea hypoxia during sleep.

Yet, another advantage of the present invention is that it provides for an anti-snoring and obstructive sleep apnea combination device fabricated from a thermoplastic material (elastomeric resin) with or without metal component, which is shaped to fit the anatomy of the oral cavity, tongue, and the soft palate.

An extra benefit of the present invention is that it provides for an anti-snoring and obstructive sleep apnea combined device, which is moldable after immersion in hot water so that it adapted by the user to have a comfortable and individualized fit.

An additional benefit of the present invention is that it provides for an anti-snoring and obstructive sleep apnea device that be coated with therapeutic agents that prevent and treat bad breath (halitosis) and used to treat the disease afflictions of the tongue, palate and other regions of the oral cavity. The therapeutic agents delivered via a syringe through the three-way stopcock provided in the device after placement of the device in the mouth before going to sleep.

Another advantage of the present device 220 is that the appropriate therapeutic agents coated inside the device to treat disease affliction of the tongue.

An added advantage of the present invention is that it provides an intra-oral dental overlay structure—incisors teeth receptacles or pockets used to displace the lower jaw to the comfortable level and at the same time supports the tongue against the user's palate to keep the palate from reverberating during mouth breathing preventing snoring and obstructive sleep apnea.

A further plus of the present invention is that it provides for an anti-snoring and obstructive sleep apnea device which is easily used, stored, cleaned, and mass-produced, economically thus making it affordable for millions who suffer from snoring with or without obstructive sleep apnea.

It is another object of this invention to allow the user of said device to keep it on the tongue; so as to facilitate talking, yawning, coughing, clearing the throat and oral secretions including regurgitated food or stomach acid secretions. After clearing the mouth, one can wash the mouth with water and antiseptic solution with device inside the oral cavity or after its removal and then reinsert into the mouth. The use of said device has the ability to pull it out of the mouth, and place it back with ease.

Numerous modifications; alternative arrangements of the described steps and examples given herein may be devised by those skilled in the art without departing from the spirit and the scope of the present invention. The appended claims are intended to cover such modifications and arrangements. Thus, the present invention has been previously described with particularity and detail. This is presently deemed to be the most practical and preferred embodiments of the invention. The invention will be apparent to those of ordinary skill in the art that numerous modifications, including, but not limited to, variations in size, materials, shape, form, function, manner of procedure, assembly, and the use may be made.

What is claimed is:

1. An anti-snoring and anti-obstructive sleep apnea oral device comprising:
    an oral elastic tongue glove adapted to removably cover a free moving portion of a tongue;
    at least one suction cup disposed on a portion of said tongue glove adapted to contact a portion of a hard palate; wherein said device holds said tongue of a user firmly without allowing backwards movement; and
    a vacuum creating syringe and cannula attached to a tip portion of said device wherein a vacuum is created between said tongue glove and said tongue holding it firmly without allowing said tongue to move backwards; a second suction cup disposed on an upper inner portion of said tongue glove; a third suction cup disposed on a lower inside surface of said tongue glove and a first plate disposed on an upper surface of said tongue glove wherein said first and second suction cups are attached therein; and a second plate disposed on a lower surface of said tongue glove wherein said third suction cup is attached therein.

2. An anti-snoring and anti-obstructive sleep apnea oral device comprising:
    a tongue glove adapted to removably cover a free moving portion of a tongue;
    a first suction cup disposed on an upper outer portion of said tongue glove adapted to contact a portion of a hard palate; and
    a vacuum creating syringe and cannula attached to a tip portion of said tongue glove wherein a vacuum is created within said tongue glove and said tongue to hold said tongue securely within said tongue glove; a second suction cup disposed on an upper inner portion of said tongue glove; a third suction cup disposed on a lower inside surface of said tongue glove and a first plate disposed on an upper surface of said tongue glove wherein said first and second suction cups are attached therein; and a second plate disposed on a lower surface of said tongue glove wherein said third suction cup is attached therein.

3. The anti-snoring and anti-obstructive sleep apnea device according to claim 2 further comprising a third suction cup disposed on a lower inside surface of said tongue glove.

4. The anti-snoring and anti-obstructive sleep apnea device according to claim 2, wherein said suction cups are further secured with a dental adhesive.

5. The anti-snoring and anti-obstructive sleep apnea device according to claim 2, further comprising:
- a string having a first end attached at a tip portion of said tongue glove; and
- said string having a second end extending out of a mouth opening of a user wherein said string is adapted to prevent said tongue glove from being accidentally swallowed.

6. The anti-snoring and anti-obstructive sleep apnea device according to claim 2 wherein said tongue glove is manufactured in selected sizes to match the physical dimensions of a user.

* * * * *